United States Patent [19]
Campbell et al.

[11] Patent Number: 5,275,005
[45] Date of Patent: Jan. 4, 1994

[54] GAS PROCESSING

[75] Inventors: Roy E. Campbell; John D. Wilkinson; Hank M. Hudson, all of Midland, Tex.

[73] Assignee: Elcor Corporation, Dallas, Tex.

[21] Appl. No.: 983,884

[22] Filed: Dec. 1, 1992

[51] Int. Cl.⁵ .............................................. F25J 3/02
[52] U.S. Cl. ................................. 62/24; 62/25; 62/27; 62/28; 62/32; 62/36; 62/42
[58] Field of Search .................. 62/24, 25, 27, 28, 32, 62/36, 42

[56] References Cited

U.S. PATENT DOCUMENTS

| | | |
|---|---|---|
| 2,603,310 | 7/1952 | Gilmore ........................ 62/25 X |
| 2,880,592 | 4/1959 | Davidson ........................ 62/25 |
| 4,061,481 | 12/1977 | Campbell et al. . |
| 4,157,904 | 6/1979 | Campbell et al. . |
| 4,171,964 | 10/1979 | Campbell et al. . |
| 4,251,249 | 2/1981 | Gulsby ........................... 62/28 |
| 4,278,457 | 7/1981 | Campbell et al. . |
| 4,368,061 | 1/1983 | Mestrallet et al. ............. 62/28 |
| 4,453,958 | 6/1984 | Gulsby et al. . |
| 4,592,766 | 6/1986 | Kumman et al. ............. 62/25 X |
| 4,596,588 | 6/1986 | Cook . |
| 4,600,421 | 7/1986 | Kummann ..................... 62/25 |
| 4,617,039 | 10/1986 | Buck . |
| 4,657,571 | 4/1987 | Gazzi ............................ 62/27 X |
| 4,676,812 | 6/1987 | Kummann ..................... 62/24 |
| 4,687,499 | 8/1987 | Aghili ........................... 62/24 |
| 4,698,081 | 10/1987 | Aghili ........................... 62/24 |
| 4,711,651 | 12/1987 | Sharma et al. ............... 62/24 X |
| 4,718,927 | 1/1988 | Bauer et al. .................. 62/24 X |
| 4,720,294 | 1/1988 | Lucadamo et al. ........... 62/28 X |
| 4,738,699 | 4/1988 | Apffel ........................... 62/24 X |
| 4,752,312 | 6/1988 | Prible ............................ 62/25 |
| 4,793,841 | 12/1988 | Burr .............................. 62/27 |
| 4,851,020 | 7/1989 | Montgomery, IV .......... 62/24 |
| 4,854,955 | 8/1989 | Campbell et al. ............. 62/24 |
| 4,869,740 | 9/1989 | Campbell et al. ............. 62/32 X |
| 4,881,960 | 11/1989 | Ranke et al. .................. 62/27 X |
| 4,889,545 | 12/1989 | Campbell et al. ............. 62/24 |
| 5,114,451 | 5/1992 | Rambo et al. ................. 62/24 |

FOREIGN PATENT DOCUMENTS

| | | |
|---|---|---|
| 1606828 | 11/1990 | U.S.S.R. ....................... 62/24 |
| 2102931 | 2/1983 | United Kingdom ........... 62/24 |

Primary Examiner—Henry A. Bennet
Assistant Examiner—C. Kilner
Attorney, Agent, or Firm—Brumbaugh, Graves, Donohue & Raymond

[57] ABSTRACT

A process for the recovery of C₂ components (ethylene and/or ethane) and heavier hydrocarbon components from a gas stream containing a significant quantity of components more volatile than methane (e.g., hydrogen, nitrogen, and/or others) is disclosed. The cooled, partially condensed hydrocarbon bearing gas stream is separated into a vapor containing substantial quantities of the component(s) more volatile than methane and a liquid containing predominantly hydrocarbons. The vapor is expanded to the distillation column pressure and then supplied to the column at an upper mid-column feed position. The liquid is expanded to column pressure and supplied to the column at a lower mid-column feed position. A recycle stream is withdrawn from the column at a point below the upper mid-column feed position where the bulk of the volatile components are supplied to the column. The recycle stream is compressed and cooled so that a substantial portion is condensed and then supplied to the column as reflux at the top column feed position. The major portion of this reflux is liquid methane which allows the recovery of a significant portion of the C₂ and heavier components that are in the vapors in the upper section of the distillation column. The distillation column overhead vapor contains predominantly methane and the more volatile components The major portion of the desired components is recovered in the distillation column bottom liquid product.

16 Claims, 5 Drawing Sheets

GAS PROCESSING

BACKGROUND OF THE INVENTION

This invention provides an improved process for separating a hydrocarbon bearing gas stream containing significant quantities of components more volatile than methane (e.g., hydrogen, nitrogen, etc.) into two fractions: one fraction contains predominantly methane and the more volatile components and the second fraction contains the recovered desirable ethylene/ethane and heavier hydrocarbons components.

Ethylene/ethane, propylene/propane and heavier hydrocarbons can be recovered from a variety of gases, such as natural gas, refinery gas and synthetic gas streams obtained from other hydrocarbon materials such as coal, crude oil, naphtha, oil shale, tar sands and lignite. Hydrocarbon bearing gas typically contains components more volatile than methane (e.g., hydrogen, nitrogen, etc.) and often unsaturated hydrocarbons (e.g., ethylene, propylene, etc.) in addition to methane, ethane and hydrocarbons of higher molecular weight such as propane, butane and pentane. Sulfur-containing gases and carbon dioxide are also sometimes present. The present invention is generally concerned with the recovery of ethylene/ethane and heavier ($C_2+$) hydrocarbons from such gas streams.

Recent changes in ethylene demand have created increased markets for ethylene and derivative products. In addition, fluctuations in the prices of both natural gas and its NGL constituents have increased the incremental value of ethane and heavier components as liquid products. These market conditions have resulted in a demand for processes which can provide high ethylene recovery and more efficient recoveries of all these products. Available processes for separating these materials include those based upon cooling and refrigeration of gas, oil absorption and refrigerated oil absorption. Additionally, cryogenic processes have become popular because of the availability of economical equipment which produces power while simultaneously expanding and extracting heat from the gas being processed. Depending upon the pressure of the gas source, the richness ($C_2+$ content) of the gas and the desired end products, each of these processes or a combination thereof may be employed.

The cryogenic expansion process is now generally preferred for ethylene/ethane recovery because it provides maximum simplicity with ease of start up, operating flexibility, good efficiency, safety and good reliability. U.S. Pat. Nos. 4,061,481, 4,157,904, 4,171,964, 4,27S,457 and 4,617,039 describe relevant processes.

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_2+$ components. Depending on the richness of the gas and the amount of liquid formed, the high-pressure liquids may be expanded to a lower pressure and fractionated. The vaporization occurring during expansion of the liquid results in further cooling of the stream. Under some conditions, pre-cooling the high pressure liquid prior to the expansion may be desirable in order to further lower the temperature resulting from the expansion. The expanded stream, comprising a mixture of liquid and vapor, is fractionated in a distillation (demethanizer) column.

If the feed gas is not totally condensed (typically it is not), the vapor remaining from the partial condensation is passed through a work expansion machine or engine, or an expansion valve, to a lower pressure at which additional liquids are condensed as a result of further cooling of the stream. The pressure after expansion is usually the same as the pressure at which the distillation column is operated. The combined vapor-liquid phases resulting from the expansion are supplied as feed to the column.

In the column, the expansion-cooled stream(s) is (are) distilled to separate residual methane, nitrogen, and other volatile gases as overhead vapor from the desired ethylene/ethane, propylene/propane and heavier components as bottom liquid product.

In the ideal operation of such a separation process, the residue gas leaving the process will contain substantially all of the methane and more volatile components in the feed gas with essentially none of the heavier hydrocarbon components and the bottoms fraction leaving the demethanizer will contain substantially all of the heavier components with essentially no methane or more volatile components. In practice, however, this ideal situation is not obtained for the reason that the conventional demethanizer is operated largely as a stripping column. The residue gas from the process, therefore, typically comprises vapors leaving the top fractionation stage of the column, together with vapors not subjected to any rectification step. Considerable losses of ethylene/ethane ($C_2$) occur because the top liquid feed contains substantial quantities of $C_2+$ components, resulting in corresponding equilibrium quantities of $C_2+$ components in the vapors leaving the top fractionation stage of the demethanizer. This problem is exacerbated if the gas stream(s) being processed contain relatively large quantities of components more volatile than methane (e.g., nitrogen, hydrogen, etc.), because the volatile vapors rising up the column strip $C_2+$ components from the liquids flowing downward. The loss of the desirable $C_2+$ components could be significantly reduced if the rising vapors could be brought into contact with a significant quantity of liquid (reflux), containing very little $C_2+$ components; that is, reflux capable of absorbing the $C_2+$ components from the vapors. The present invention provides the means for achieving this objective and significantly improving the recovery of the desired products.

In accordance with the present invention, it has been found that ethylene recoveries in excess of 99 percent can be obtained. In addition, the present invention makes possible higher ethylene and ethane recoveries (up to several percentage points higher) than prior art processes with the same energy requirements. The present invention is particularly advantageous when processing feed gas that contains more than 10 mole % of components more volatile than methane (e.g., hydrogen, nitrogen, etc.).

For a better understanding of the present invention, reference is made to the following examples and drawings. Referring to the drawings.

For each of the above figures, a table is provided summarizing flow rates calculated for representative process conditions. In the tables appearing herein, the values for flow rates (in pound moles per hour) have been rounded to the nearest whole number for convenience. Temperatures indicated are approximate values rounded to the nearest degree. It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

EXAMPLE 1

The first example illustrates the improvement of the present invention over a prior art process when recovering ethylene, ethane and heavier components from a refinery gas or similar hydrocarbon bearing stream with a high hydrogen content. The example stream contains 22 mole % hydrogen.

DESCRIPTION OF THE PRIOR ART

Figure 1:
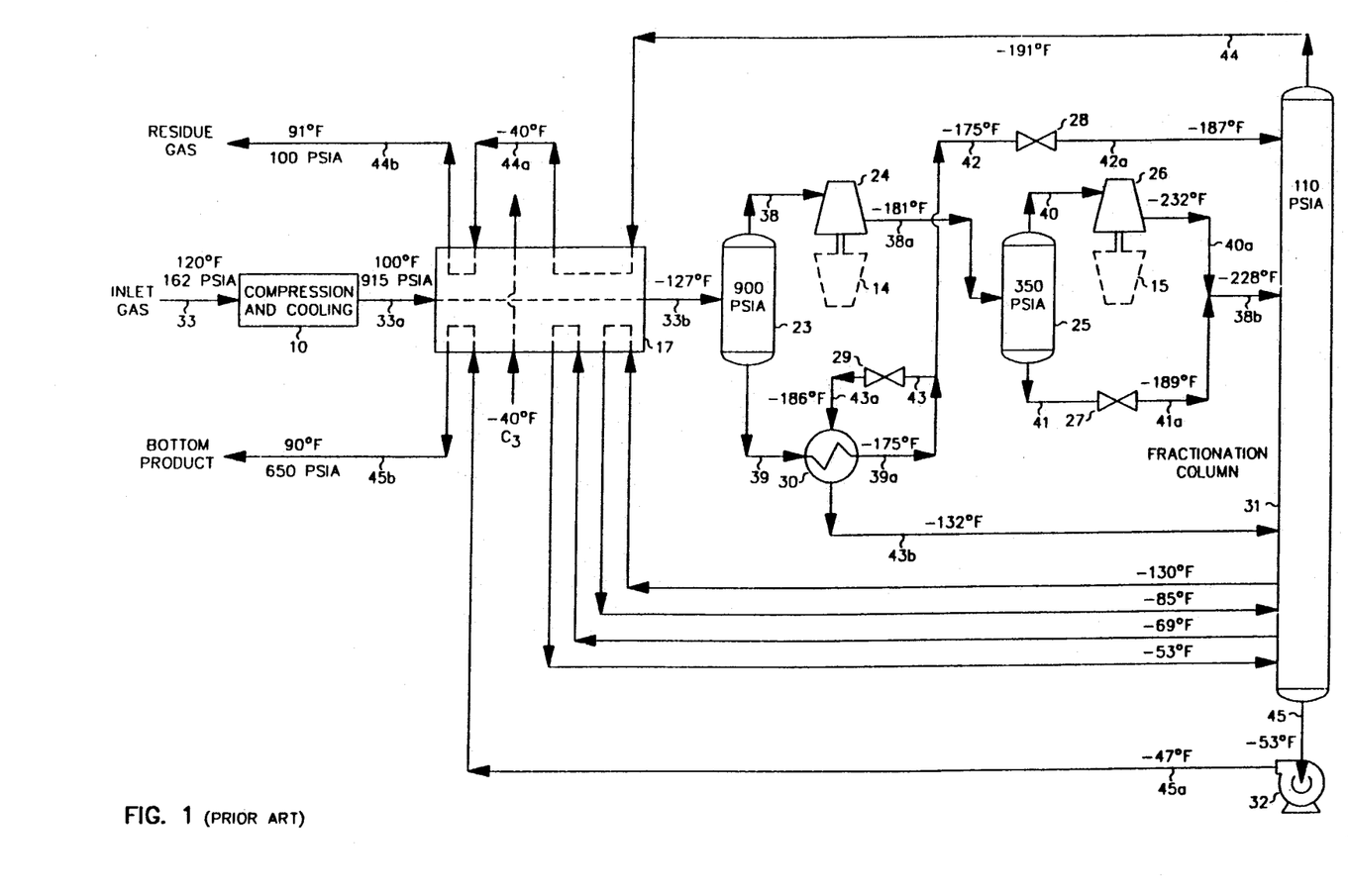
FIG. 1 is a flow diagram of a cryogenic expansion refinery gas processing plant of the prior art according to U.S. Pat. No. 4,171,964 modified to include two expansion stages in series.

Referring now to FIG. 1, in a simulation of the process according to U.S. Pat. No. 4,171,964, inlet gas enters the plant at 120° F/ and 162 psia as stream 33. If the inlet gas contains a concentration of sulfur compounds and/or carbon dioxide which would prevent the product streams from meeting specifications, the sulfur compounds and/or carbon dioxide may be removed by appropriate pretreatment of the feed gas (not illustrated). In addition, the feed stream is usually dehydrated to prevent hydrate (ice) formation under cryogenic conditions. Solid desiccant has typically been used for this purpose.

Depending on the pressure at which the inlet gas (stream 33) is available, it may be compressed and cooled in one or more stages (equipment section 10). For this example, only two stages would be required. The high pressure feed gas leaving the final stage of compression and cooling flows to the heat exchanger section 17 at 100° F. and 915 psia, stream 33a.

The feed stream 33b is cooled in heat exchanger section 17 by heat exchange with residue gas (stream 44), bottom product (stream 45a), propane refrigerant and demethanizer liquids. The cooled stream 33b enters a first separator 23 at −127° F. and 900 psia, and the vapor (stream 38) is separated from the condensed liquid (stream 39).

The vapor from first separator 23 (stream 38) enters work expansion machine 24 in which mechanical energy is extracted from this portion of the high pressure feed. Machine 24 expands the vapor substantially isentropically from a pressure of about 900 psia to a pressure of about 350 psia, with the work expansion cooling the expanded stream 38a to a temperature of approximately −181° F. The typical commercially available expanders are capable of recovering on the order of 80–85% of the work theoretically available in an ideal isentropic expansion. The work recovered is often used to drive a centrifugal compressor (such as item 14), that can be used to compress inlet gas (stream 33, reducing the compression requirements in equipment section 10) or to re-compress the residue gas (stream 44b), for example. The expanded and partially condensed stream 38a enters a second separator 25 where the vapor (stream 40) is separated from the condensed liquid (stream 41)

Vapor from second separator 25 (stream 40) enters work expansion machine 26 in which mechanical energy is extracted from this portion of the feed. Machine 26 expands the vapor substantially isentropically from a pressure of about 350 psia to the operating pressure of the demethanizer (about 110 psia), with the work expansion cooling the expanded stream 40a to a temperature of approximately −232° F.

It should be recognized by those skilled in the art that the work expansion in expansion machines 24 and 26 can sometimes be accomplished in a single work expansion device. The decision to use more than one expansion machine is dictated by the mechanical limitations of the expansion devices themselves, such as the maximum pressure drop which can be taken across a single unit, the maximum liquid formation which can be tolerated, or other factors.

Liquid from second separator 25 (stream 41) is flash expanded through an appropriate expansion device, such as expansion valve 27, to the operating pressure of the demethanizer. During expansion, a portion of the stream will vaporize, resulting in cooling of the total stream. In the process illustrated in FIG. 1, the expanded stream 41a leaving expansion valve 27 reaches a temperature of −189° F. The expanded streams (40a and 41a) are recombined as partially condensed stream 38b at −228° F. and supplied to the demethanizer at an upper mid-column feed point.

The liquid from first separator 23 (stream 39) is cooled to −175° F. by heat exchange with expanded stream 43a at −186° F. in liquid subcooler 30. The subcooled liquid (stream 39a) is split into two portions. Approximately 57% of the subcooled liquid (stream 42) is flash expanded through expansion valve 28 to a pressure of 110 psia and is thereby cooled to −187° F. (stream 42a). The expanded substantially condensed stream 42a is supplied to the demethanizer as the top column feed. The remaining 43% of the subcooled liquid (stream 43) is flash expanded through expansion valve 29 to a pressure of 115 psia and is thereby cooled to −186° F. The resulting substantially condensed stream 43b is warmed to −132° F. by heat exchange with high pressure separator liquid 39 at −127° F. in liquid subcooler 30. The warmed partially condensed stream 43b is supplied to the demethanizer at a lower mid-column feed point.

The demethanizer in fractionation tower 31 is a conventional distillation column containing a plurality of vertically spaced trays, one or more packed beds, or some combination of trays and packing. As is often the case in gas processing plants, the fractionation tower consists of two sections. The upper section is a separator wherein the partially vaporized top feed is divided into its respective vapor and liquid portions, and wherein the vapor rising from the lower distillation or demethanizing section is combined with the vapor portion of the top feed to form the cold residue gas stream 44 which exits the top of the tower. The lower demethanizing section contains the trays and/or packing and provides the necessary contact between the liquids falling downward and the vapors rising upward. The demethanizing section also includes reboilers which heat and vaporize a portion of the liquids flowing down the column to provide the stripping vapors which flow up the column.

The bottom product stream 45 exits the bottom of the tower at −53° F., based on a typical specification of a methane mole fraction of 0.02 in the bottom product. Product pump 32 increases the pressure of the bottom product stream to 655 psia. This higher pressure is sufficient to maintain the bottom product in the liquid phase while it is warmed in its service as a cooling medium for inlet gas The bottom product stream is warmed to −47° F. (stream 45a) as it passes through pump 32. High pressure bottom product 45a is further warmed to 90° F. (stream 45b) by heat exchange with inlet gas in heat exchanger section 17.

The residue gas 44 passes countercurrently to the incoming feed gas in heat exchanger section 17 where it is heated from −191° F. to −40° F. (stream 44a) and from −40° F. to 91° F. (stream 44b). It should be noted by those skilled in the art that heat exchanger section 17 can be a single multi-service plate fin type heat exchanger, a plurality of appropriately arranged shell and tube type heat exchangers, or a combination of both types, which is at the discretion of the designer.

Figure 2:
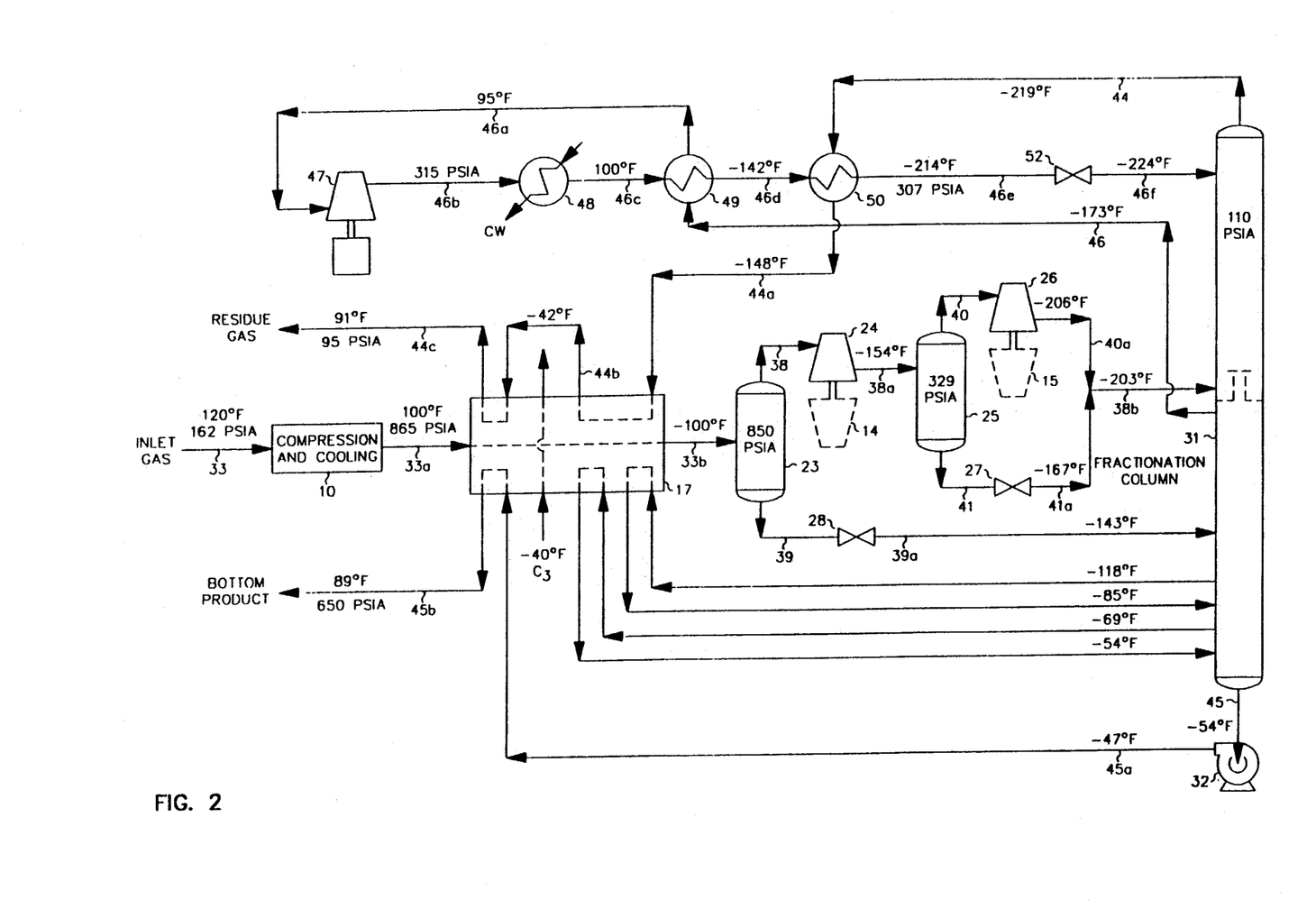
FIG. 2 is a flow diagram of a refinery gas processing plant in accordance with the present invention.

A summary of stream flow rates and energy consumption for the process illustrated in FIG. 1 is set forth in the table below:

first separator 23 at −100° F. and 850 psia, and the vapor (stream 38) is separated from the condensed liquid (stream 39).

The vapor from first separator 23 (stream 38) enters work expansion machine 24 in which mechanical energy is extracted from this portion of the high pressure feed. Machine 24 expands the vapor substantially isentropically from a pressure of about 850 psia to a pressure of about 329 psia, with the work expansion cooling the expanded stream 38a to a temperature of approximately −154° F. The expanded and partially condensed stream 38a enters a second separator 25 where the vapor (stream 40) is separated from the condensed liquid (stream 41).

Vapor from second separator 25 (stream 40) enters work expansion machine 26 in which mechanical energy is extracted from this portion of the feed. Machine 26 expands the vapor substantially isentropically from a pressure of about 329 psia to the operating pressure (about 110 psia) of the demethanizer (fractionation column 31), with the work expansion cooling the expanded stream 40a to a temperature of approximately −206° F. Liquid from second separator 25 (stream 41) is flash expanded through expansion valve 27 to a pressure of 110 psia and is thereby cooled to −167° F. (stream 41a). The expanded streams, 40a and 41a, are recombined as partially condensed stream 38b at −203° F. and supplied to the demethanizer at an upper mid-column feed point.

The liquid from first separator 23 (stream 39) is flash expanded through expansion valve 28 to the operating

| Stream Flow Summary - Lb. Moles/Hr. | | | | | | | | |
|---|---|---|---|---|---|---|---|---|
| Stream | 33 | 38 | 39 | 42 | 43 | 44 | 45 | Recoveries* |
| Hydrogen | 891 | 816 | 75 | 43 | 32 | 891 | 0 | |
| Nitrogen | 102 | 73 | 29 | 17 | 12 | 102 | 0 | |
| Carbon Dioxide | 15 | 10 | 5 | 3 | 2 | 15 | 0 | |
| Methane | 1595 | 506 | 1089 | 624 | 465 | 1566 | 29 | |
| Ethylene | 383 | 21 | 362 | 208 | 154 | 21 | 362 | 94.45% |
| Ethane | 674 | 18 | 656 | 376 | 280 | 13 | 661 | 98.13% |
| Propylene | 198 | 1 | 197 | 113 | 84 | 0 | 198 | 99.88% |
| Propane | 92 | 0 | 92 | 52 | 40 | 0 | 92 | 99.93% |
| Butanes+ | 107 | 0 | 107 | 61 | 46 | 0 | 107 | |
| Total | 4057 | 1445 | 2612 | 1497 | 1115 | 2608 | 1449 | |
| Horsepower | | | | | | | | |
| Inlet Compression | | | 4030 | | | | | |
| Refrigeration | | | 889 | | | | | |
| Total horsepower | | | 4919 | | | | | |

*(Based on un-rounded flow rates)

DESCRIPTION OF THE INVENTION

FIG. 2 illustrates a flow diagram of a process in accordance with the present invention. The feed gas composition and conditions considered in the process presented in FIG. 2 are the same as those in FIG. 1. Accordingly, FIG. 2 can be compared with the FIG. 1 process to illustrate the advantages of the present invention.

In the simulation of the FIG. 2 process, gas enters at 120° F. and a pressure of 162 psia (stream 33). It is compressed and cooled (equipment section 10) as discussed for the FIG. 1 process. The high pressure feed gas leaving the final stage of compression and cooling flows to the heat exchanger section 17 at 100° F. and 865 psia, stream 33a.

The feed stream 33b is cooled in heat exchanger section 17 by heat exchange with residue gas (stream 44a), bottom product (stream 45a), propane refrigerant and demethanizer liquids. The cooled stream 33b enters a pressure of the demethanizer and is thereby cooled to −143° F. The expanded stream 39a is supplied to the demethanizer at a lower mid-column feed point.

A portion of the demethanizer vapor (recycle stream 46) is withdrawn from the column at a point below the upper mid-column feed point ultimately to become the top demethanizer feed. This recycle gas stream 46 is warmed from −173° F. to 95° F. (stream 46a) by heat exchange with high pressure recycle gas (stream 46c) at 100° F. in exchanger 49.

Warmed recycle gas stream 46a is compressed to 315 psia (stream 46b) by recycle compressor 47, which is driven by a supplemental power source. The high pressure recycle gas is cooled to 100° F. (stream 46c) with cooling water in exchanger 48, and further cooled to −142° F. (stream 46d) by heat exchange with the low pressure recycle gas (stream 46) in exchanger 49. Recycle gas 46d passes countercurrently to the cold demethanizer overhead vapor (stream 44) in heat exchanger 50 where it is cooled to −214° F. (stream 46e). The cooled recycle stream 46e is expanded through an appropriate expansion device, such as expansion valve 52, to the demethanizer operating pressure of about 110 psia. In the 46f reaches a temperature of −224° F. The partially condensed recycle stream 46f is supplied to the demethanizer as the top column feed.

The bottom product stream 45 exits the bottom of the tower at −54° F., based on a typical specification of a methane mole fraction of 0.02 in the bottom product. Product pump 32 pumps product stream 45 to a pressure of 655 psia (stream 45a), thereby warming it to −47° F. High pressure product 45a is further warmed to 89° F. (stream 45b) by heat exchange with inlet gas at 100° F. in heat exchanger section 17.

The demethanizer overhead vapor (stream 44) passes countercurrently to the recycle gas in heat exchanger 50 where it is warmed from −219° F. to 148° F. (stream 44a). The warmed residue gas 44a passes countercurrently to the incoming feed gas in heat exchanger section 17 where it is further warmed to 91° F. (stream 44c).

A summary of stream flow rates and energy consumption for the process illustrated in FIG. 2 is set forth in the table below:

| Stream Flow Summary - Lb. Moles/Hr. | | | | | | |
|---|---|---|---|---|---|---|
| Stream | 33 | 38 | 39 | 46 | 44 | 45 | Recoveries* |
| Hydrogen | 891 | 834 | 57 | 23 | 891 | 0 | |
| Nitrogen | 102 | 82 | 20 | 8 | 102 | 0 | |
| Carbon Dioxide | 15 | 12 | 3 | 1 | 15 | 0 | |
| Methane | 1595 | 767 | 828 | 381 | 1565 | 30 | |
| Ethylene | 383 | 49 | 334 | 16 | 3 | 380 | 99.33% |
| Ethane | 674 | 48 | 626 | 4 | 0 | 674 | 99.98% |
| Propylene | 198 | 3 | 195 | 0 | 0 | 198 | 100.00% |
| Propane | 92 | 1 | 91 | 0 | 0 | 92 | 100.00% |
| Butanes+ | 107 | 0 | 107 | 0 | 0 | 107 | |
| Total | 4057 | 1796 | 2261 | 433 | 2576 | 1481 | |
| Horsepower | | | | | | | |
| Inlet Compression | | | 3731 | | | | |
| Refrigeration | | | 864 | | | | |
| Recycle Compression | | | 314 | | | | |
| Total horsepower | | | 4909 | | | | |

*(Based on un-rounded flow rates)

As discussed in a previous section, BACKGROUND OF THE INVENTION, considerable losses of ethylene/ethane ($C_2$) occur in conventional demethanizers because the top liquid feed contains substantial quantities of $C_{2+}$ components and corresponding equilibrium quantities of these components remain in the demethanizer overhead vapor. The prior art illustrated in FIG. 1 uses feed inversion and autorefrigeration to provide a very cold liquid reflux stream as the top column feed. The corresponding improvement in the top stage equilibrium conditions results in higher $C_{2+}$ recovery than that for systems with the expander outlet as the top feed. However, the reflux in FIG. 1 contains significant quantities of $C_{2+}$ components which limit the $C_2$ recovery. The present invention illustrated in FIG. 2 provides a methane-rich reflux containing very little volatile (i.e., hydrogen and/or nitrogen) or $C_{2+}$ components by withdrawing a side vapor stream from the demethanizer at a point below the feed position where the bulk of the more volatile components are supplied to the column. Supplying this predominantly liquid methane reflux to the demethanizer's top stage significantly improves the recovery of the desired hydrocarbon products.

Comparison of the recovery levels displayed in the tables for the FIG. 1 and FIG. 2 processes shows that the present invention improves ethylene recovery from 94.45% to 9.33% and ethane recovery from 98.13% to 99.98%. Comparison of the two tables further shows that the improvement in yields is achieved at essentially the same horsepower (utility) requirements. When the present invention is employed, not only do the ethylene and ethane recoveries increase considerably over those of the prior art process, liquid recovery efficiency also increases by 5.4 percent (in terms of ethylene recovered per unit of horsepower expended).

Figure 3:
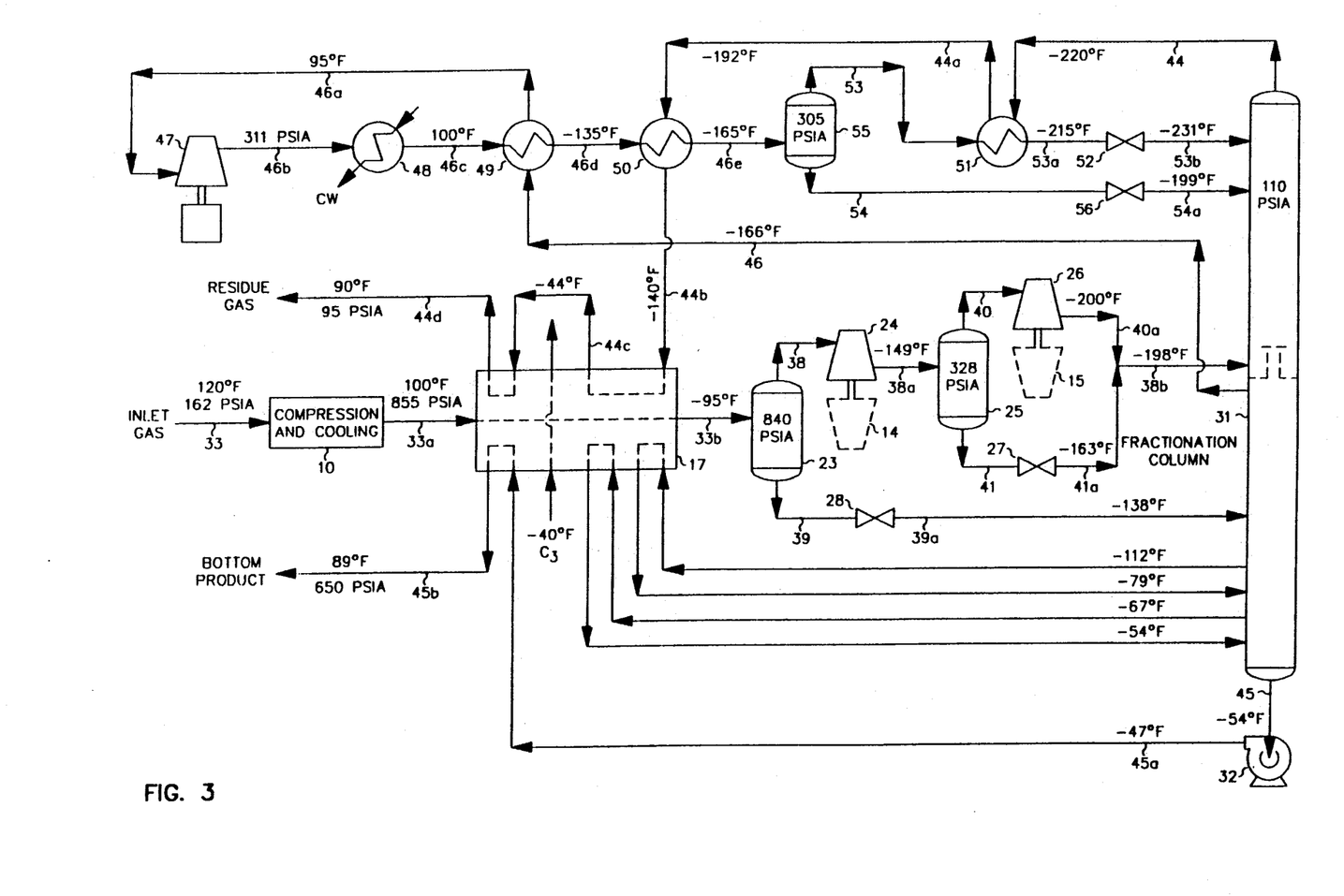
FIG. 3 is a flow diagram illustrating an alternative means of application of the present invention to a refinery gas stream.

FIG. 2 represents the preferred embodiment of the present invention for the conditions shown. Additional improvement of ethylene recovery can be achieved with the use of a separator on the recycle (reflux) stream, as illustrated in the FIG. 3 process. The feed gas composition and conditions considered in the process presented in FIG. 3 are the same as those in FIGS. 1 and 2. Accordingly, FIG. 3 can be compared with the FIG. 1 process to illustrate the advantages of the present invention.

In the simulation of the FIG. 3 process, gas enters at 120° F. and a pressure of 162 psia (stream 33). It is compressed and cooled (equipment section 10) as discussed previously. The high pressure feed gas leaving the final stage of compression and cooling flows to the heat exchanger section 17 at 100° F. and 855 psia, stream 33a.

The feed stream 33a is cooled in heat exchanger section 17 by heat exchange with residue gas (stream 44b), bottom product (stream 45a), propane refrigerant and demethanizer liquids. The cooled stream 33b enters a first separator 23 at −95° F. and 840 psia, and the vapor (stream 38) is separated from the condensed liquid (stream 39).

The vapor from first separator 23 (stream 38) enters work expansion machine 24 in which mechanical energy is extracted from this portion of the high pressure feed. Machine 24 expands the vapor substantially isentropically from a pressure of about 840 psia to a pressure of about 328 psia, with the work expansion cooling the expanded stream 38a to a temperature of approximately −149° F. The expanded and partially condensed stream 38a enters a second separator 25 where the vapor (stream 40) is separated from the condensed liquid (stream 41).

Vapor from second separator 25 (stream 40) enters work expansion machine 26 in which mechanical energy is extracted from this portion of the feed. Machine 26 expands the vapor substantially isentropically from a pressure of about 328 psia to the operating pressure (about 110 psia) of the demethanizer (fractionation column 31), with the work expansion cooling the expanded stream 40a to a temperature of approximately −200° F. Liquid from second separator 25 (stream 41) is flash expanded through expansion valve 27 to a pressure of 110 psia and is thereby cooled to −163° F. (stream 41a). The expanded streams, 40a and 41a, are recombined as partially condensed stream 38b at −198° F. and supplied to the demethanizer at an upper mid-column feed point.

The liquid from first separator 23 (stream 39) is flash expanded through expansion valve 28 to the operating pressure of the demethanizer and is thereby cooled to −138° F. The expanded stream 39a is supplied to the demethanizer at a lower mid-column feed point.

A portion of the demethanizer vapor (recycle stream 46) is withdrawn from the column at a point below the upper mid-column feed point. This recycle gas stream A summary of stream flow rates and energy consumption for the process illustrated in FIG. 3 is set forth in the table below:

| Stream Flow Summary - Lb. Moles/Hr. | | | | | | | | | |
|---|---|---|---|---|---|---|---|---|---|
| Stream | 33 | 38 | 39 | 46 | 53 | 54 | 44 | 45 | Recoveries* |
| Hydrogen | 891 | 837 | 54 | 28 | 27 | 1 | 891 | 0 | |
| Nitrogen | 102 | 84 | 18 | 10 | 7 | 3 | 102 | 0 | |
| Carbon Dioxide | 15 | 12 | 3 | 2 | 1 | 1 | 15 | 0 | |
| Methane | 1595 | 818 | 777 | 471 | 173 | 298 | 1565 | 30 | |
| Ethylene | 383 | 56 | 327 | 28 | 2 | 26 | 1 | 382 | 99.70% |
| Ethane | 674 | 56 | 618 | 6 | 0 | 6 | 0 | 674 | 99.99% |
| Propylene | 198 | 4 | 194 | 0 | 0 | 0 | 0 | 198 | 100.00% |
| Propane | 92 | 1 | 91 | 0 | 0 | 0 | 0 | 92 | 100.00% |
| Butanes+ | 107 | 0 | 107 | 0 | 0 | 0 | 0 | 107 | |
| Total | 4057 | 1868 | 2189 | 545 | 210 | 335 | 2574 | 1483 | |
| Horsepower | | | | | | | | | |
| Inlet Compression | | | | 3668 | | | | | |
| Refrigeration | | | | 857 | | | | | |
| Recycle Compression | | | | 390 | | | | | |
| Total horsepower | | | | 4915 | | | | | |

*(Based on un-rounded flow rates)

46 is warmed from −166° F. to 95° F. (stream 46a) by heat exchange with high gas (stream 46c) at 100° F. in pressure recycle exchanger 49.

Warmed recycle gas stream 46a is compressed to 311 psia (stream 46b) by recycle compressor 47, which is driven by a supplemental power source. The high pressure recycle gas is cooled to 100° F. (stream 46c) in exchanger 48, and further cooled to −135° F. (stream 46d) by heat exchange with the low pressure recycle gas (stream 46) in exchanger 49. Recycle gas 46d passes countercurrently to the cool demethanizer overhead vapor (stream 44a) in heat exchanger 50 where it is cooled to −165° F. (stream 46e) and enters recycle separator 55 where the vapor (stream 53) is separated from the condensed liquid (stream 54).

The recycle separator vapor 53 is cooled to −215° F. (stream 53a) by heat exchange with cold demethanizer overhead vapor (stream 44) at −220° F. in exchanger 51. The cooled and partially condensed stream 53a is expanded through expansion valve 52 to the demethanizer operating pressure of about 110 psia, thereby cooling it to −231° F. (stream 53b). Stream 53b is then supplied to the demethanizer as the top column feed. The recycle separator liquid (stream 54) is expanded through expansion valve 56 to 110 psia and thereby cooled to −199° F. The expanded stream 54a is delivered to the demethanizer at the first mid-column feed point.

The bottom product stream 45 exits the bottom of the tower at −54° F., based on a typical specification of a methane mole fraction of 0.02 in the bottom product. Product pump 32 pumps product stream 45 to a pressure of 655, psia (stream 45a), thereby warming it to −47° F. High pressure product 45a is further warmed to 89° F. (stream 45b) by heat exchange with inlet gas at 100° F. in heat exchanger section 17.

The demethanizer overhead vapor (stream 44) passes countercurrently to the recycle separator vapor in heat exchanger 51 where it is warmed from −220° F. to −192° F. (stream 44a) and countercurrently to the recycle gas in heat exchange 50 where it is warmed to −140° F. (stream 44b). The warmed residue gas 44b then passes countercurrently to the incoming feed gas in heat exchanger section 17 where it is further warmed to 90° F. (stream 44d).

The partial condensation of the recycle gas in exchanger 50 and removal of the condensate by recycle separator 55 in the FIG. 3 process provides a top liquid feed to the demethanizer with a $C_2+$ content significantly lower than that in the FIG. 2 embodiment of the present invention. Comparison of the recovery levels displayed in the tables for the FIG. 2 and FIG. 3 processes shows that utilizing the additional equipment improves the ethylene recovery from 99.33% to 99.70%. The ethane recovery increases slightly from 99.98% to 99.99% and the propylene and propane recoveries remain at 100.00%. These two embodiments of the present invention have essentially the same horsepower (utility) requirements.

EXAMPLE 2

The second example illustrates the improvement of the present invention over a prior art process when recovering ethane and heavier components from a natural gas or similar hydrocarbon bearing stream with a high nitrogen content. The sample stream contains 17.5 mole % nitrogen.

DESCRIPTION OF THE PRIOR ART

Figure 4:
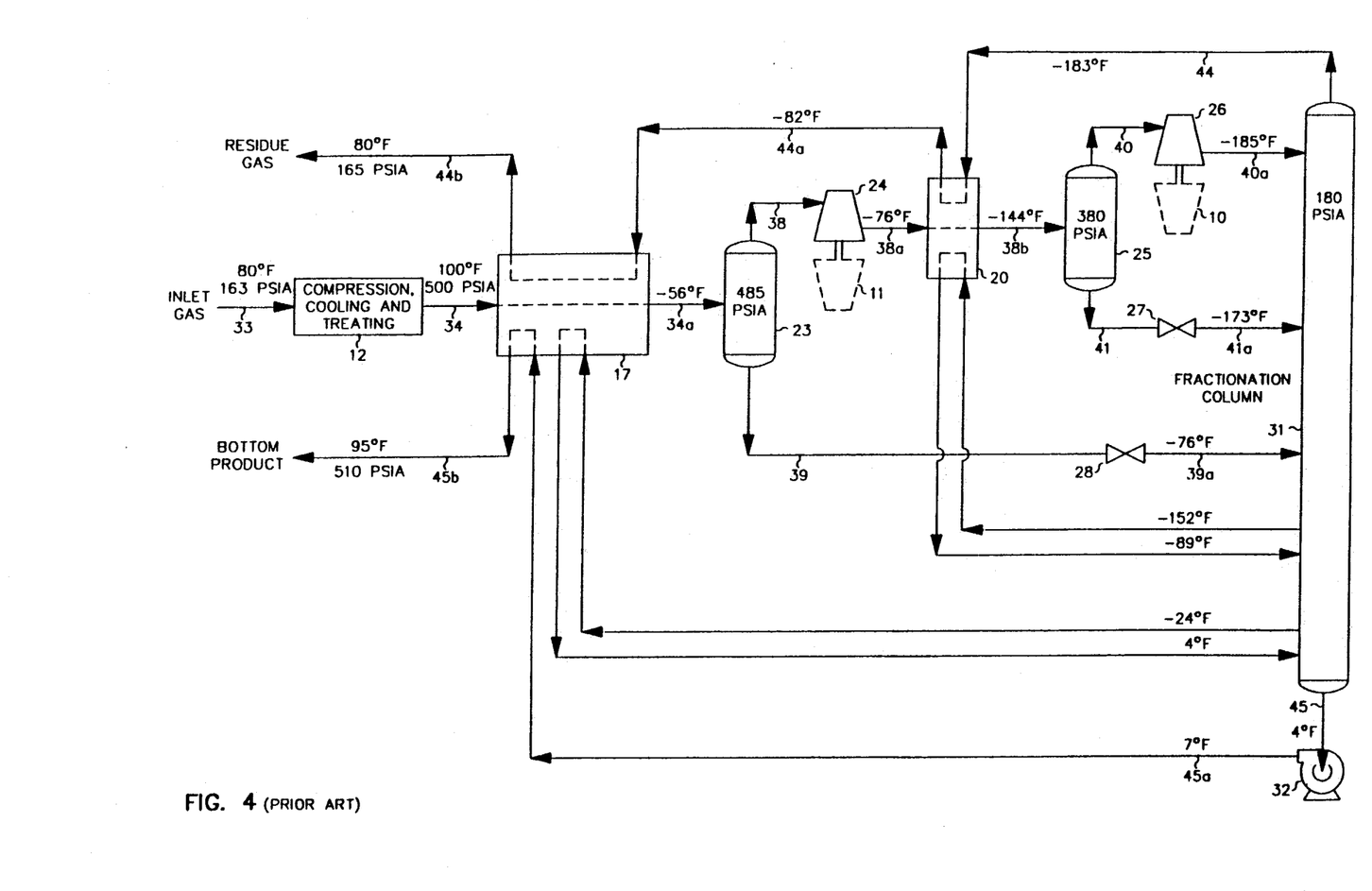
FIG. 4 is a flow diagram of a cryogenic expansion natural gas processing plant of an alternative prior art process according to U.S. Pat. No. 4,061,481.

Referring now to FIG. 4, in a simulation of the process according to U.S. Pat. No. 4,061,481, natural gas enters the plant at 80° F. and a pressure of 163 psia as stream 33. The inlet gas is compressed and cooled in one or more stages (equipment section 12). If the inlet gas contains a concentration of carbon dioxide which would cause formation of solids in the cold temperature sections of the process, the carbon dioxide is removed by appropriate pretreatment of the feed gas in equipment section 12. In addition, the feed stream is usually dehydrated to prevent hydrate (ice) formation under cryogenic conditions. Solid desiccant has typically been used for this purpose. The treated, dehydrated high pressure feed gas (stream 34) flows to heat exchanger section 17 at 100° F. and 500 psia.

The feed stream 34 is cooled in heat exchanger section 17 by heat exchange with residue gas (stream 44a), NGL product (stream 45a) and demethanizer liquids. The feed stream 34a enters a first separator 23 at −56° F. and 485 psia, and the vapor (stream 38) is separated from the condensed liquid (stream 39).

The vapor from first separator 23 (stream 38) enters work expansion machine 24 in which mechanical energy is extracted from this portion of the high pressure feed. Machine 24 expands the vapor substantially isentropically from a pressure of about 485 psia to a pressure of about 385 psia, with the work expansion cooling the expanded stream 38a to a temperature of approximately −76° F. Stream 38a is further cooled to −144° F. (stream 38b) by heat exchange with cold residue gas at −183° F. (stream 44) and demethanizer liquids at −152° F. in heat exchanger section 20. Stream 38b enters a second separator 25 and the vapor (stream 40) is separated from the condensed liquid (stream 41).

Vapor from second separator 25 (stream 40) enters work expansion machine 26 in which mechanical energy is extracted from this portion of the feed. Machine 26 expands the vapor substantially isentropically from a pressure of about 380 psia to the operating pressure of the demethanizer (about 180 psia), with the work expansion cooling the expanded stream 40a to a temperature of approximately −185° F. The expanded partially condensed stream 40a is introduced to the demethanizer at the top feed point.

Liquid from second separator 25 (stream 41) is flash expanded through expansion valve 27 to the operating pressure of the demethanizer and is thereby cooled to −173° F. (stream 41a). Expanded stream 41a is supplied to the demethanizer at an upper mid-column feed point.

The liquid from first separator 23 (stream 39) is flash expanded through expansion valve 28 to the operating pressure of the demethanizer. The expanded stream 39a reaches a temperature of −76° F. and is supplied to the demethanizer at a lower mid-column feed point.

The demethanizer bottom product (stream 45) exits the bottom of the tower at 4° F., based on a typical specification of a methane to ethane ratio of 0.025:1 on a molar basis in the bottom product. NGL pump 32 pumps product stream 45 to a pressure of 515 psia (stream 45a), thereby warming it to 7° F. High pressure product 45a is further warmed to 95° F. by heat exchange with inlet gas at 100° F. in heat exchanger section 17.

The demethanizer overhead vapor (stream 44) passes countercurrently to the expanded stream in heat exchanger section 20 where it is warmed from −183° F. to −82° F. (stream 44a). The warmed residue gas 44a passes countercurrently to the incoming feed gas in heat exchanger section 17 where it is further warmed to 80° F. (stream 44b).

A summary of stream flow rates and energy consumption for the process illustrated in FIG. 4 is set forth in the table below:

DESCRIPTION OF THE INVENTION

Figure 5:
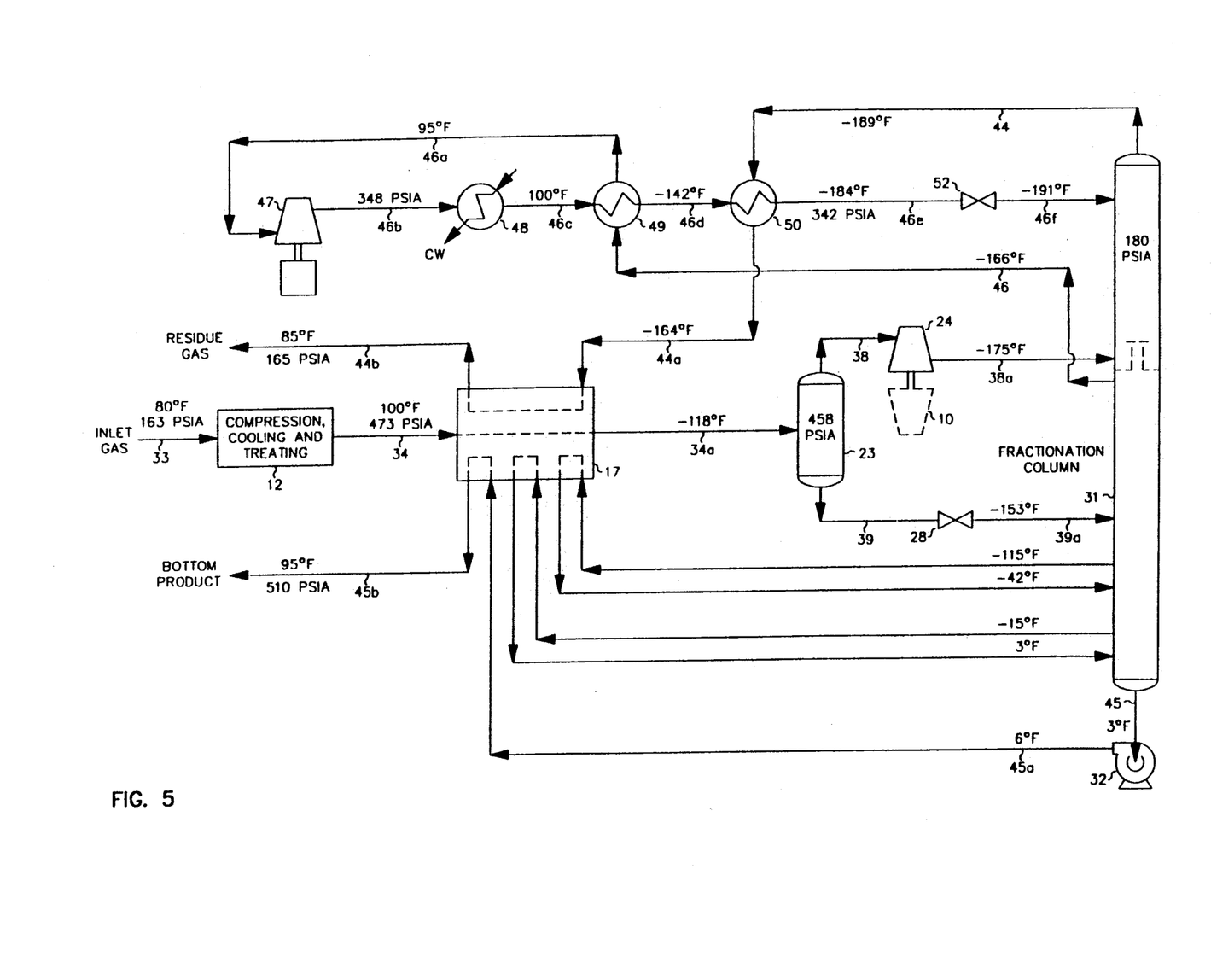
FIG. 5 is a flow diagram of a natural gas processing plant in accordance with the present invention.

FIG. 5 illustrates a flow diagram of a process in accordance with the present invention. The composition and conditions of the feed gas considered in the process presented in FIG. 5 are the same as those in FIG. 4. Accordingly, FIG. 5 can be compared with the FIG. 4 process to illustrate the advantages of the present invention.

In the simulation of the FIG. 5 process, natural gas enters at 80° F. and a pressure of 163 psia (stream 33). It is compressed and cooled as discussed previously, treated if necessary, then dehydrated in equipment section 12. The treated, dehydrated high pressure feed gas (stream 34) flows to heat exchanger section 17 at 100° F. and 473 psia.

The feed stream 34 is cooled in heat exchanger section 17 by heat exchange with residue gas (stream 44a), NGL product (stream 45a) and demethanizer liquids. The cooled feed stream 34a enters separator 23 at −118° F. and 458 psia, and the vapor (stream 38) is separated from the condensed liquid (stream 39).

The vapor from separator 23 (stream 38) enters work expansion machine 24 in which mechanical energy is extracted from this portion of the feed. Machine 24 expands the vapor substantially isentropically from a pressure of about 458 psia to the operating pressure (about 180 psia) of the demethanizer (fractionation column 31), with the work expansion cooling the expanded stream 38a to a temperature of approximately −175° F. The expanded partially condensed stream 38a is supplied to the column at an upper mid-column feed point.

The liquid from separator 23 (stream 39) is flash expanded through expansion valve 28 to the operating pressure of the demethanizer. The expanded stream 39a reaches a temperature of about −153° F. and is supplied to the demethanizer at a lower mid-column feed point.

A portion of the demethanizer vapor (recycle stream 46) is withdrawn from the column at a point below the upper mid-column feed point ultimately to become the top demethanizer feed. This recycle gas stream 46 is warmed from −166° F. to 95° F. (stream 46a) by heat exchange with high pressure recycle gas (stream 46c) at 100° F. in exchanger 49.

Warmed recycle gas stream 46a is compressed to 348 psia (stream 46b) by recycle compressor 47, which is driven by a supplemental power source. The high pressure recycle gas is cooled to 100° F. (stream 46c) in exchanger 48, and further cooled to −142° F. (stream 46d) by heat exchange with the low pressure recycle gas (stream 46) in exchanger 49. Recycle gas 46d passes countercurrently to the cold demethanizer overhead vapor (stream 44) in heat exchanger 50 where it is cooled to −184° F. (stream 46e). The cooled recycle

| Stream Flow Summary - Lb. Moles/Hr. | | | | | | | | | |
|---|---|---|---|---|---|---|---|---|---|
| Stream | 33 | 34 | 38 | 39 | 40 | 41 | 44 | 45 | Recoveries* |
| Nitrogen | 1400 | 1400 | 1398 | 2 | 1347 | 51 | 1400 | 0 | |
| Carbon Dioxide | 53 | 2 | 2 | 0 | 1 | 1 | 1 | 1 | |
| Methane | 6006 | 6006 | 5971 | 35 | 5016 | 955 | 5998 | 8 | |
| Ethane | 371 | 371 | 350 | 21 | 84 | 266 | 32 | 339 | 91.31% |
| Propane | 117 | 117 | 90 | 27 | 3 | 87 | 0 | 117 | 99.90% |
| Butanes+ | 68 | 68 | 22 | 46 | 0 | 22 | 0 | 68 | |
| Total | 8015 | 7964 | 7833 | 131 | 6451 | 1382 | 7431 | 533 | |
| Horsepower | | | | | | | | | |
| Inlet Compression | | | 4505 | | | | | | |

*(Based on un-rounded flow rates)

stream 46e is expanded through an appropriate expansion device, such as expansion valve 52, to the demethanizer operating pressure of about 180 psia. In the process illustrated in FIG. 5, the expanded recycle stream 46f reaches a temperature of −191° F. The partially condensed recycle stream is supplied to the demethanizer as the top column feed.

The bottom product stream 45 exits the bottom of the tower at 3° F., based on a typical specification of a methane to ethane ratio of 0.025:1 on a molar basis in the bottom product. NGL pump 32 pumps product stream 45 to a pressure of 515 psia (stream 45a), thereby warming it to 6° F. High pressure product 45a is further warmed to 95° F. by heat exchange with inlet gas at 100° F. in heat exchanger section 17.

The demethanizer overhead vapor (stream 44) passes countercurrently to the recycle gas in heat exchanger 50 where it is warmed from −189° F. to −164° F. (stream 44a). The warmed residue gas 44a passes countercurrently to the incoming feed gas in heat exchanger section 17 where it is further warmed to 85° F. (stream 44b).

A summary of stream flow rates and energy consumption for the process illustrated in FIG. 5 is set forth in the table below:

| Stream Flow Summary - Lb. Moles/Hr. | | | | | | | | |
|---|---|---|---|---|---|---|---|---|
| Stream | 33 | 34 | 38 | 39 | 46 | 44 | 45 | Recoveries* |
| Nitrogen | 1400 | 1400 | 1377 | 23 | 24 | 1400 | 0 | |
| Carbon Dioxide | 53 | 2 | 2 | 0 | 0 | 1 | 1 | |
| Methane | 6006 | 6006 | 5562 | 444 | 578 | 5997 | 9 | |
| Ethane | 371 | 371 | 176 | 195 | 8 | 12 | 359 | 96.78% |
| Propane | 117 | 117 | 14 | 103 | 0 | 0 | 117 | 100.00% |
| Butanes+ | 68 | 68 | 1 | 67 | 0 | 0 | 68 | |
| Total | 8015 | 7964 | 7132 | 832 | 610 | 7410 | 554 | |
| Horsepower | | | | | | | | |
| Inlet Compression | | | 4280 | | | | | |
| Recycle Compression | | | 226 | | | | | |
| Total horsepower | | | 4506 | | | | | |

*(Based on un-rounded flow rates)

As in the embodiments shown in FIG. 2 and FIG. 3, the present invention's side draw recycle stream provides reflux with a much lower fraction of $C_2+$ components than the prior art, which significantly improves the recovery of the desired products. Comparison of the recovery levels displayed in the tables for FIG. 4 and FIG. 5 shows that the present invention improves ethane recovery from 91.31% to 96.78% and propane recovery from 99.90% to 100.00%. Comparison of the two tables further shows that the improvement in yields is achieved at essentially the same horsepower (utility) requirements. When the present invention is employed, not only does the ethane recovery increase substantially over that of the prior art process, but liquid recovery efficiency also increases by 5.9 percent (in terms of ethane recovered per unit of horsepower expended).

The embodiments shown in FIGS. 2, 3, and 5 can also be used when it is desirable to recover only the $C_3$ components and heavier components ($C_2$ component rejection). This is accomplished by appropriate adjustment of the column feed rates and conditions. Moreover, the embodiments of FIGS. 2, 3 and 5 can be modified to provide for fractionation in more than one vessel. Examples of such fractionation schemes are disclosed in U.S. Pat. Nos. 4,453,958 and 4,596,588. When the present invention is employed in such multiple vessel fractionation schemes, the recycle stream is withdrawn from a region of one of the fractionation sections wherein the temperature in that region is warmer than the temperature of at least one of the feed streams to the overall fractionation system.

While there have been described what are believed to be preferred embodiments of the invention, those skilled in the art will recognize that other and further modifications may be made thereto, e.g., to adapt the invention to various conditions, types of feed or other requirements without departing from the spirit of the present invention as defined by the following claims.

We claim:

1. In a process for the separation of a gas, stream containing methane and components more volatile than methane, $C_2$ components, $C_2$ components and heavier hydrocarbon components, into (i) a volatile residue gas fraction containing a major portion of said methane and components more volatile than methane and (ii) a relatively less volatile fraction containing a major portion of said $C_2$ components, $C_3$ components and heavier components in which process    (a) said gas is cooled under pressure to provide a cooled stream;

(b) said cooled stream is expanded to a lower pressure whereby it is further cooled; and    (c) said further cooled stream is supplied to at least one fractionation section in at least one feed stream for fractionation at said lower pressure whereby the major portion of said $C_2$ components, $C_3$ components and heavier hydrocarbon components is recovered in said relatively less volatile fraction;

the improvement wherein

(1) a recycle stream is withdrawn from a region of said fractionation section below at least one of said feed streams;

(2) said recycle stream is compressed and thereafter said compressed recycle stream is cooled sufficiently to substantially condense it;

(3) said substantially condensed compressed recycle stream is expanded and thereafter supplied to said fractionation section at a top feed position;

(4) the quantity and pressure of said compressed recycle stream and the temperatures of said feed streams are effective to maintain the overhead temperature of said fractionation section at a temperature whereby the major portion of said $C_2$ components, $C_3$ components and heavier hydrocarbon components is recovered in said relatively less volatile fraction.

2. In a process for the separation of a gas stream containing methane and components more volatile than methane, $C_2$ components, $C_3$ components and heavier hydrocarbon components into (i) a volatile residue gas fraction containing a major portion of said methane, $C_2$ components and components more volatile than methane and (ii) a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is supplied to at least one fractionation section in at least one feed stream for fractionation at said lower pressure whereby the major portion of said $C_3$ components and heavier hydrocarbon components is recovered in said relatively less volatile fraction;

the improvement wherein (1) a recycle stream is withdrawn from a region of said fractionation section below at least one of said feed streams;

(2) said recycle stream is compressed and thereafter said compressed recycle stream is cooled sufficiently to substantially condense it;

(3) said substantially condensed compressed recycle stream is expanded and thereafter supplied to said fractionation section at a top feed position;

(4) the quantity and pressure of said compressed recycle stream and the temperatures of said feed streams are effective to maintain the overhead temperature of said fractionation section at a temperature whereby the major portion of said $C_3$ components and heavier hydrocarbon components is recovered in said relatively less volatile fraction.

3. The improvement according to claim 1 or 2 wherein said recycle stream is heated prior to compression.

4. In a process for the separation of a gas stream containing methane and components more volatile than methane, $C_2$ components, $C_3$ components and heavier hydrocarbon components into (i) a volatile residue gas fraction containing a major portion of said methane and components more volatile than methane and (ii) a relatively less volatile fraction containing a major portion of said $C_2$ components, $C_3$ components and heavier components, in which process (a) said gas is cooled under pressure to provide a cooled stream;

(b) said cooled stream is expanded to a lower pressure whereby it is further cooled; and (c) said further cooled stream is supplied to at least one fractionation section in at least one feed stream for fractionation at said lower pressure whereby the major portion of said $C_2$ components, $C_3$ components and heavier hydrocarbon components is recovered in said relatively less volatile fraction;

the improvement wherein (1) a recycle stream is withdrawn from a region of said fractionation section below at least one of said feed streams;

(2) said recycle stream is compressed and thereafter said compressed recycle stream is cooled sufficiently to partially condense it;

(3) said partially condensed compressed recycle stream is separated thereby to provide a vapor stream and a condensed stream;

(4) said condensed stream is expanded and thereafter supplied to said fractionation section at an upper mid-column feed position;

(5) said vapor stream is cooled sufficiently to substantially condense it;

(6) said substantially condensed vapor stream is expanded and thereafter supplied to said fractionation section at a top feed position;

(7) the quantity and pressure of said compressed recycle stream and the temperatures of said feed streams are effective to maintain the overhead temperature of said fractionation section at a temperature whereby the major portion of said $C_2$ components, $C_3$ components and heavier hydrocarbon components is recovered in said relatively less volatile fraction.

5. In a process for the separation of a gas stream containing methane and components more volatile than methane, $C_2$ components, $C_3$ components and heavier hydrocarbon components into (i) a volatile residue gas fraction containing a major portion of said methane, $C_2$ components and components more volatile than methane and (ii) a relatively less volatile fraction containing a major portion of said $C_3$ components and heavier components, in which process (a) said gas is cooled under pressure to provide a cooled stream;

(b) said cooled stream is expanded to a lower pressure whereby it is further cooled; and (c) said further cooled stream is supplied to at least one fractionation section in at least one feed stream for fractionation at said lower pressure whereby the major portion of said $C_3$ components and heavier hydrocarbon components is recovered in said relatively less volatile fraction;

the improvement wherein (1) a recycle stream is withdrawn from a region of said fractionation section below at least one of said feed streams;

(2) said recycle stream is compressed and thereafter said compressed recycle stream is cooled sufficiently to partially condense it;

(3) said partially condensed compressed recycle stream is separated thereby to provide a vapor stream and a condensed stream;

(4) said condensed stream is expanded and thereafter supplied to said fractionation section at an upper mid-column feed position;

(5) said vapor stream is cooled sufficiently to substantially condense it;

(6) said substantially condensed vapor stream is expanded and thereafter supplied to said fractionation section at a top feed position;

(7) the quantity and pressure of said compressed recycle stream and the temperatures of said feed streams are effective to maintain the overhead temperature of said fractionation section at a temperature whereby the major portion of said $C_3$ components and heavier hydrocarbon components is recovered in said relatively less volatile fraction.

6. The improvement according to claim 4 or 5 wherein said recycle stream is heated prior to compression.

7. The improvement according to claim 1, 2, 4 or 5 wherein there is more than one fractionation section, and wherein the recycle stream is withdrawn from a region of one of said sections wherein the temperature in said region is warmer than the temperature of at least one of the feed streams to the fractionation sections.

8. The improvement according to claim 7 wherein said recycle stream is heated prior to compression.

9. In an apparatus for the separation of a gas stream containing methane and components more volatile than methane, $C_2$ components, $C_3$ components and heavier hydrocarbon components, into (i) a volatile residue gas fraction containing a major portion of said methane and components more volatile than methane and (ii) a relatively less volatile fraction containing a major portion of said $C_2$ components, $C_3$ components and heavier components, in said apparatus there being (a) a first cooling means to cool said gas under pressure connected to provide a cooled stream under pressure;

(b) a first expansion means connected to receive at least a portion of said cooled stream under pressure and to further expand it to a lower pressure, whereby said stream is further cooled; and (c) at least one fractionation section connected to said first expansion means to receive the further cooled stream therefrom in at least one feed;

the improvement wherein said apparatus includes (1) withdrawing means connected to said fractionation section to receive a recycle stream from a region of said fractionation section below at least one of said feed streams;

(2) compressing means connected to said withdrawing means to receive said recycle stream and compress it;

(3) second cooling means connected to said compressing means to receive said compressed recycle stream and cool it sufficiently to substantially condense it;

(4) second expansion means connected to said second cooling means to receive said substantially condensed compressed recycle stream and expand it, said second expansion means being further connected to said fractionation section to supply said expanded substantially condensed recycle stream to said fractionation section at a top feed position; and (5) control means adapted to regulate the quantity and pressure of said compressed recycle stream and the temperatures of said feed streams to maintain the overhead temperature of said fractionation section at a temperature whereby the major portion of said $C_2$ components, $C_3$ components and heavier hydrocarbon components is recovered in said relatively less volatile fraction.

10. In an apparatus for the separation of a gas stream containing methane and components more volatile than methane, $C_2$ components, $C_3$ components and heavier hydrocarbon components, into (i) a volatile residue gas fraction containing a major portion of said methane, $C_2$ components and components more volatile than methane and (ii) a relatively less volatile fraction containing a major portion of said $C_3$ components and heavier components, in said apparatus there being (a) a first cooling means to cool said gas under pressure connected to provide a cooled stream under pressure;

(b) a first expansion means connected to receive at least a portion of said cooled stream under pressure and to further expand it to a lower pressure, whereby said stream is further cooled; and (c) at least one fractionation section connected to said first expansion means to receive the further cooled stream therefrom in at least one feed;

the improvement wherein said apparatus includes (1) withdrawing means connected to said fractionation section to receive a recycle stream from a region of said fractionation section below at least one of said feed streams;

(2) compressing means connected to said withdrawing means to receive said recycle stream and compress it;

(3) second cooling means connected to said compressing means to receive said compressed recycle stream and cool it sufficiently to substantially condense it;

(4) second expansion means connected to said second cooling means to receive said substantially condensed compressed recycle stream and expand it, said second expansion means being further connected to said fractionation section to supply said expanded substantially condensed recycle stream to said fractionation section at a top feed position; and (5) control means adapted to regulate the quantity and pressure of said compressed recycle stream and the temperatures of said feed streams to maintain the overhead temperature of said fractionation section at a temperature whereby the major portion of said $C_3$ components and heavier hydrocarbon components is recovered in said relatively less volatile fraction.

11. The improvement according to claim 9 or 10 wherein said apparatus includes heating means connected to said withdrawing means to receive said recycle stream and heat it, said heating means being further connected to said compressing means to supply said heated recycle stream thereto.

12. In an apparatus for the separation of a gas stream containing methane and components more volatile than methane, $C_2$ components, $C_3$ components and heavier hydrocarbon components, into (i) a volatile residue gas fraction containing a major portion of said methane and components more volatile than methane and (ii) a relatively less volatile fraction containing a major portion of said $C_2$ components, $C_3$ components and heavier components, in said apparatus there being (a) a first cooling means to cool said gas under pressure connected to provide a cooled stream under pressure;

(b) a first expansion means connected to receive at least a portion of said cooled stream under pressure and to further expand it to a lower pressure, whereby said stream is further cooled; and (c) at least one fractionation section connected to said first expansion means to receive the further cooled stream therefrom in at least one feed;

the improvement wherein said apparatus includes (1) withdrawing means connected to said fractionation section to receive a recycle stream from a region of said fractionation section below at least one of said feed streams;

(2) compressing means connected to said withdrawing means to receive said recycle stream and compress it;

(3) second cooling means connected to said compressing means to receive said compressed recycle stream and cool it sufficiently to partially condense it;

(4) separating means connected to said second cooling means to receive said partially condensed compressed recycle stream and separate it into a vapor stream and a condensed stream;

(5) second expansion means connected to said separating means to receive said condensed stream and expand it, said second expansion means being further connected to said fractionation section to supply said expanded condensed stream to said fractionation section at an upper mid-column feed position;

(6) third cooling means connected to said separating means to receive said vapor stream and cool it sufficiently to substantially condense it;

(7) third expansion means connected to said third cooling means to receive said substantially condensed vapor stream and expand it, said third expansion means being further connected to said fractionation section to supply said expanded substantially condensed vapor stream to said fractionation section at a top feed position; and (8) control means adapted to regulate the quantity and pressure of said compressed recycle stream and the temperatures of said feed streams to maintain the overhead temperature of said fractionation section at a temperature whereby the major portion of said $C_2$ components, $C_3$ components and heavier hydrocarbon components is recovered in said relatively less volatile fraction.

13. In an apparatus for the separation of a gas stream containing methane and components more volatile than methane, $C_2$ components, $C_3$ components and heavier hydrocarbon components, into (i) a volatile residue gas fraction containing a major portion of said methane, $C_2$ components and components more volatile than methane and (ii) a relatively less volatile fraction containing a major portion of said $C_3$ components and heavier components, in said apparatus there being (a) a first cooling means to cool said gas under pressure connected to provide a cooled stream under pressure;

(b) a first expansion means connected to receive at least a portion of said cooled stream under pressure and to further expand it to a lower pressure, whereby said stream is further cooled; and (c) at least one fractionation section connected to said first expansion means to receive the further cooled stream therefrom in at least one feed;

the improvement wherein said apparatus includes (1) withdrawing means connected to said fractionation section to receive a recycle stream from a region of said fractionation section below at least one of said feed streams;

(2) compressing means connected to said withdrawing means to receive said recycle stream and compress it;

(3) second cooling means connected to said compressing means to receive said compressed recycle stream and cool it sufficiently to partially condense it;

(4) separating means connected to said second cooling means to receive said partially condensed compressed recycle stream and separate it into a vapor stream and a condensed stream;

(5) second expansion means connected to said separating means to receive said condensed stream and expand it, said second expansion means being further connected to said fractionation section to supply said expanded condensed stream to said fractionation section at an upper mid-column feed position;

(6) third cooling means connected to said separating means to receive said vapor stream and cool it sufficiently to substantially condense it;

(7) third expansion means connected to said third cooling means to receive said substantially condensed vapor stream and expand it, said third expansion means being further connected to said fractionation section to supply said expanded substantially condensed vapor stream to said fractionation section at a top feed position; and (8) control means adapted to regulate the quantity and pressure of said compressed recycle stream and the temperatures of said feed streams to maintain the overhead temperature of said fractionation section at a temperature whereby the major portion of said $C_3$ components and heavier hydrocarbon components is recovered in said relatively less volatile fraction.

14. The improvement according to claim 12 or 13 wherein said apparatus includes heating means connected to said withdrawing means to receive said recycle stream and heat it, said heating means being further connected to said compressing means to supply said heated recycle stream thereto.

15. The improvement according to claim 9, 10, 12 or 13 wherein said apparatus includes more than one fractionation section and wherein said withdrawing means are connected to one of said sections to withdraw said recycle stream from a region of the section wherein the temperature in the region is warmer than the temperature of at least one of the feed streams to the fractionation sections.

16. The improvement according to claim 15 wherein said apparatus includes heating means connected to said withdrawing means to receive said recycle stream and heat it, said heating means being further connected to said compressing means to supply said heated recycle stream thereto.

* * * * *

UNITED STATES PATENT AND TRADEMARK OFFICE
CERTIFICATE OF CORRECTION

PATENT NO. : 5,275,005

DATED : January 4, 1994

INVENTOR(S) : Campbell et al.

It is certified that error appears in the above-identified patent and that said Letters Patent is hereby corrected as shown below:

Col. 1, line 52, "4,27S,457" should read --4,278,457--;

Col. 2, line 36, "corresponding" should follow immediately after "resulting in" on the preceding line;

Col. 3, line 37, "120° F/" should read --120° F--;

Col. 4, line 52, "43b" should read --43a--;

Col. 5, line 65, "33b" should read --33a--;

Col. 7, line 6, "46f" should read --process illustrated in FIG. 2, the expanded recycle stream 46f--;

Col. 7, line 19, "148° F." should read --148° F--;

Col. 8, line 6, "9.33%" should read --99.33%--;

UNITED STATES PATENT AND TRADEMARK OFFICE
CERTIFICATE OF CORRECTION

PATENT NO. : 5,275,005

DATED : January 4, 1994

INVENTOR(S) : Campbell et al.

It is certified that error appears in the above-indentified patent and that said Letters Patent is hereby corrected as shown below:

Col. 9, lines 25-26, "gas (stream 46c) at 100° F. in pressure recycle exchanger 49" should read --pressure recycle gas (stream 46c) at 100° F. in exchanger 49--;

Col. 9, line 64, "exchange" should read --exchanger--;

Col. 14, line 12, "gas, stream" should read --gas stream--; and

Col. 14, line 14, "$C_2$" (second occurrence) should read --$C_3$--.

Signed and Sealed this

Second Day of August, 1994

Attest:

BRUCE LEHMAN

Attesting Officer     Commissioner of Patents and Trademarks